United States Patent [19]

Bonin et al.

[11] Patent Number: 4,826,874
[45] Date of Patent: May 2, 1989

[54] USE OF PYRETHROIDS IN A POUR-ON PARASITIC METHOD

[75] Inventors: Werner Bonin, Kelkheim, Fed. Rep. of Germany; Jacques Martel, Bondy, France

[73] Assignee: Roussel Uclaf, Paris, France

[21] Appl. No.: 574,551

[22] Filed: Jan. 27, 1984

Related U.S. Application Data

[63] Continuation-in-part of Ser. No. 161,869, Jun. 23, 1980, abandoned, which is a continuation-in-part of Ser. No. 212,567, Dec. 3, 1980, abandoned.

[30] Foreign Application Priority Data

Jun. 29, 1979 [FR] France ............................... 7916892
Dec. 10, 1979 [FR] France ............................... 7930203

[51] Int. Cl.$^4$ ...................... A01N 37/34; A01N 53/00
[52] U.S. Cl. .................................... 514/521; 514/531
[58] Field of Search ................ 424/304, 306; 514/521, 514/531

[56] References Cited

U.S. PATENT DOCUMENTS

| | | |
|---|---|---|
| 3,201,677 | 9/1965 | Matthewson . |
| 3,201,777 | 9/1965 | Matthewson et al. . |
| 3,201,877 | 9/1965 | Mattewson . |
| 3,326,768 | 6/1967 | MacMillan .......................... 424/265 |
| 3,527,864 | 9/1970 | MacMillan et al. ................ 424/337 |
| 3,551,554 | 12/1970 | Herschler .................................. 424/7 |
| 3,962,458 | 6/1976 | Schrider ............................. 424/306 |
| 4,020,181 | 4/1977 | Blackman et al. .................. 424/305 |
| 4,031,239 | 6/1977 | Schrider ............................. 424/304 |
| 4,100,297 | 7/1978 | Grandadam et al. ............... 424/304 |
| 4,341,760 | 7/1982 | Matthewson ........................ 424/45 |

FOREIGN PATENT DOCUMENTS

| | | |
|---|---|---|
| 2374851 | 7/1978 | France . |
| 2384494 | 11/1978 | France ................................ 424/304 |

OTHER PUBLICATIONS

Chem. Abst. 71, 111327(X) (1969)–Datskovskii.
Chem. Abst. 84, 131.134(d) (1976)–Dedek et al.
Chem. Abst. 85, 116,592(d) (1976)–Wenzel et al.

*Primary Examiner*—Douglas W. Robinson
*Attorney, Agent, or Firm*—Bierman and Muserlian

[57] ABSTRACT

The invention is directed to combatting parasites of warm-blooded animals use cyclopropylcarboxylate compounds. The compounds are applied to a portion of the exterior surface of the animal.

18 Claims, No Drawings

USE OF PYRETHROIDS IN A POUR-ON PARASITIC METHOD

PRIOR APPLICATIONS

This application is a continuation-in-part of copending, commonly assigned U.S. patent application Ser. No. 161,869, filed June 23, 1980 and a continuation-in-part of Ser. No. 212,567, filed Dec. 3, 1980, both now abandoned.

SUMMARY OF THE INVENTION

A novel method of combatting parasites of warm-blooded animals to free the animal's body of parasites comprising applying to a portion of the exterior surface of a warm-blooded animal's body a composition containing a parasitically effective amount of at least one of the possible isomeric forms of a compund of the formula selected from the group consisting of

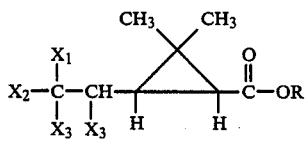

and

A—COOB        II wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is selected from the group consisting of (a) benzyl optionally substituted with at least one member of the group consisting of alkyl of 1 to 4 carbon atoms, alkenyl and alkenyloxy of 2 to 6 carbon atoms, alkadienyl of 4 to 8 carbon atoms, methylenedioxy, benzyl and halogen, (b) a group of the formula

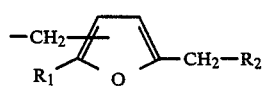

$R_1$ is selected from the group consisting of hydrogen and methyl, $R_2$ is selected from the group consisting of monocyclic aryl and —$CH_2$—C≡CH, (c) a group of the formula

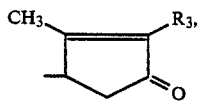

$R_3$ is aliphatic of 2 to 6 carbon atoms containing at least one double bond, (d) a group of the formula

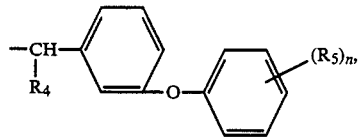

$R_4$ is selected from the group consisting of hydrogen, —CN and —C≡CH, $R_5$ is selected from the group consisting of chlorine and methyl, n is 0, 1 or 2 and (e) a compound of the group

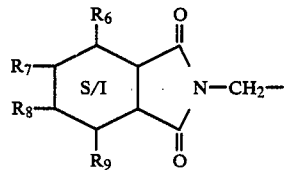

$R_6$, $R_7$, $R_8$ and $R_9$ being individually selected from the group consisting of hydrogen, chlorine and methyl and S/I indicates that the ring may be aromatic, dihydro or tetrahydro, A is selected from the group consisting of

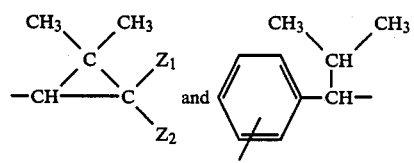

$Z_1$ and $Z_2$ are both methyl or $Z_1$ is hydrogen and $Z_2$ is

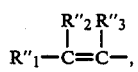

$R_3''$ is selected from the group consisting of hydrogen and halogen, $R_1''$ and $R_2''$ are individually selected from the group consisting of halogen, alkyl of 1 to 8 carbon atoms, or $R_1''$ and $R_2''$ taken together with the carbon atom to which they are attached, form a ring selected from the group consisting of cycloalkyl of 3 to 6 carbon atoms and

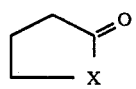

which is connected with the double bond, by the carbon atom situated in the α position of the ketone, X is selected from the group consisting of oxygen and sulfur, Y is in any position on the benzene ring and is selected from the group consisting of halogen and alkyl and alkoxy of 1 to 8 carbon atoms, m is 0, 1 or 2, B is selected from the group consisting of (1) benzyl optionally substituted with at least one member of the group consisting of alkyl of 1 to 4 carbon atoms, alkenyl and alkenyloxy of 2 to 6 carbon atoms, alkadienyl of 4 to 8 carbon atoms, methylenedioxy, benzyl and halogen

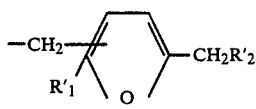 (2)

wherein $R_1'$ is selected from the group consisting of hydrogen and methyl $R_2'$ is selected from the group consisting of monocyclic aryl and $-CH_2-C\equiv CH$,

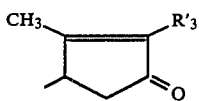 (3)

wherein $R_3'$ is an aliphatic of 2 to 6 carbon atoms containing at least one double bond,

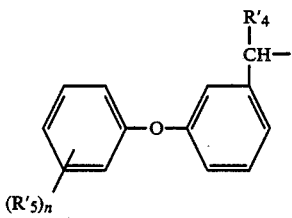 (4)

wherein $R_4'$ is seclected from the group consisting of $-CN$ and $-C\equiv CH$, $R_5'$ is selected from the group consisting of methyl and chlorine, n is o, 1 or 2 and

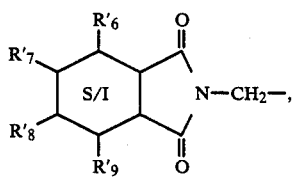 (5)

$R_6'$, $R_7'$, $R_8'$ and $R_9'$ are individually selected from the group consisting of hydrogen, chlorine and methyl and S/I indicates an aromatic ring or a dihydro or tetrahydro ring in an appropriate vehicle.

STATE OF THE ART

Related prior art, some of which describes the compounds of formula I, includes British Pat. No. 1,511,646, French Pat. No. 2,374,851, No. 2,374,849, No. 2,373,966 and No. 2,300,553, U.S. Pat. No. 3,962,458, No. 4,100,297, No. 4,136,195 and No. 4,315,943 and copending, commonly assigned U.S. patent application Ser. No. 896,574 filed Apr. 14, 1978.

OBJECTION OF THE INVENTION

It is an object of the invention to provide a novel method of treating warm-blooded animals infested with parasites.

It is another object of the invention to provide a novel method of protecting farm animals from infestation with acariens.

These and other objects and advantages of the invention will become obvious from the following detailed description.

THE INVENTION

The novel method of the invention for treating warm-blooded animals infested with parasites to free them therefrom comprises administering to a portion of the exterior of the animal's body an antiparastically effective amount of at least one compound in all of its possible isomeric forms of the formula selected from the group consisting of

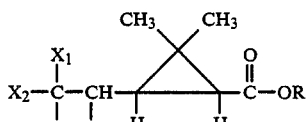 I and

ACOOB  II wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is selected from the group consisting of (a) benzyl optionally substituted with at least one member of the group consisting of alkyl of 1 to 4 carbon atoms, alkenyl and alkenyloxy of 2 to 6 carbon atoms, alkadienyl of 4 to 8 carbon atoms, methylenedioxy, benzyl and halogen, (b) a group of the formula

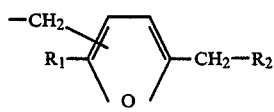

$R_1$ is selected from the group consisting of hydrogen and methyl, $R_2$ is selected from the group consisting of monocyclic aryl and $-CH_2-C\equiv CH$, (c) a group of the formula

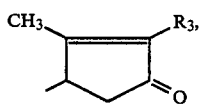

$R_3$ is aliphatic of 2 to 6 carbon atoms containing at least one double bond, (d) a group of the formula

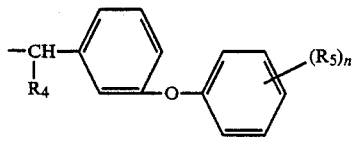

$R_4$ is selected from the group consisting of hydrogen, $-CN$ and $-C\equiv CH$, $R_5$ is selected from the group consisting of chlorine and methyl, n is 0, 1 or 2 and (e) a compound of the group

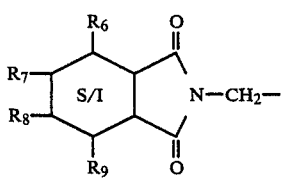

$R_6$, $R_7$, $R_8$ and $R_9$ being individually selected from the group consisting of hydrogen, chlorine and methyl and S/I indicates that the ring may be aromatic, dihydro or tetrahydro, A is selected from the group consisting of

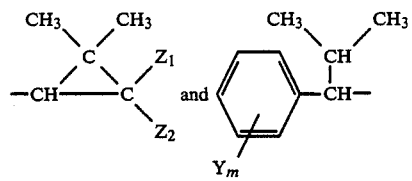

$Z_1$ and $Z_2$ are both methyl or $Z_1$ is hydrogen and $Z_2$ is

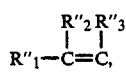

$R_3''$ is selected from the group consisting of hydrogen and halogen, $R_1''$ and $R_2''$ are individually selected from the group consisting of halogen, alkyl of 1 to 8 carbon atoms, or $R_1''$ and $R_2''$ taken together with the carbon atom to which they are attached, form a ring selected from the group consisting of cycloalkyl of 3 to 6 carbon atoms and

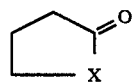

which is connected with the double bond, by the carbon atom situated in the α position of the ketone, X is selected from the group consisting of oxygen and sulfur, Y is in any position on the benzene ring and is selected from the group consisting of halogen and alkyl and alkoxy of 1 to 8 carbon atoms, m is 0, 1 or 2, B is selected from the group consisting of (1) benzyl optionally substituted with at least one member of the group consisting of alkyl of 1 to 4 carbon atoms, alkenyl and alkenyloxy of 2 to 6 carbon atoms, alkadienyl of 4 to 8 carbon atoms, methylenedioxy, benzyl and halogen,

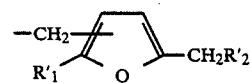

(2)

wherein $R_1'$ is selected from the group consisting of hydrogen and methyl $R_2$ is selected from the group consisting of monocyclic aryl and —CH$_2$—C≡CH,

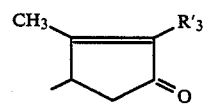

(3)

wherein $R_3'$ is an aliphatic of 2 to 6 carbon atoms containing at least one double bond,

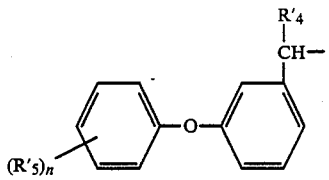

(4)

wherein $R_4'$ is selected from the group consisting of —CN and —C≡CH $R_5'$ is selected from the group consisting of methyl and chlorine, n is 0, 1 or 2 and

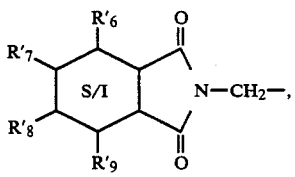

(5)

$R_6'$, $R_7'$, $R_8'$ and $R_9'$ are individually selected from the group consisting of hydrogen, chlorine and methyl and S/I indicates an aromatic ring or a dihydro or tetrahydro ring in an appropriate vehicle.

Examples of $R_2'$ is 5-benzyl-3-furyl methyl, and of $R_3'$ are vinyl, propen-1-yl, buta-1,3-dienyl and buten-1-yl and of $R_5'$ are 3-phenoxy-benzyl, α-cyano-3-phenoxy-benzyl and α-ethynyl-3-phenoxy-benzyl.

A preferred method of the invention comprises the use of compounds of formula II wherein $Z_1$ is hydrogen, $Z_2$ is

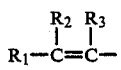

and especially wherein $R_3$ is hydrogen and $R_1$ and $R_2$ are halogen such as bromine or chlorine.

Among the preferred compounds of formula I are those wherein R is 5-benzyl-3-furylmethyl, those wherein R is

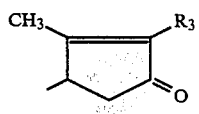

and $R_3$ is selected from the group consisting of vinyl, propen-1-yl, buta-1,3-dienyl and buten-1-yl and those wherein R is selected from the group consisting of 3-phenoxy-benzyl, α-cyano-3-phenoxy-benzyl and α-ethynyl-3-phenoxy-benzyl.

The most preferred compounds of the invention are all the possible isomers of the compound of the formula

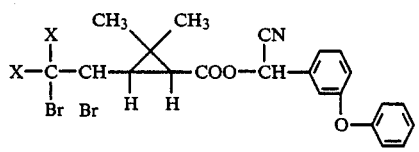

$I_A$ wherein X is selected from the group consisting of chlorine and bromine. (S)α-cyano-3-phenoxy-benzyl (1R, cis) 2,2-dimethyl-3-(2,2-dichloro-1,2-dibromoethyl)-cyclopropane-1-carboxylate called product A in the Examples and (S)α-cyano-3-phenoxy-benzyl (1R, cis) 2,2-dimethyl-3-(1,2,2,2-tetrabromoethyl)-cyclopropane-1-carboxylate are two preferred compounds which are described in Examples 1 and 2, respectively, of Belgium Pat. No. 858,894.

Examples of preferred active ingredients for the method of the invention are (S)α-cyano-3-phenoxy-benzyl (1R, cis) 2,2-dimethyl-3-(2,2-dibromovinyl)-cyclopropane-1-carboxylate, (S)α-cyano-3-phenoxy-benzyl (1R, cis) 2,2-dimethyl-3-(2,2-dichlorovinyl)-cyclopropane-1-carboxylate, 3-phenoxy-benzyl (1R, trans) 2,2-dimethyl-3-(2,2-dichlorovinyl)-cyclopropane-1-carboxylate, (RS)α-cyano-3-phenoxy-benzyl (1R, cis) 2,2-dimethyl-3-(2,2-dichlorovinyl)-cyclopropane-1-carboxylate, 5-benzyl-3-furyl-methyl (1R, trans) 2,2-dimethyl-3-cyclopentylidenemethyl-cyclopropane-1-carboxylate, racemates or optically active, cis or trans and mixtures of 5-benzyl-3-furyl-methyl chrysanthemates, 5-benzyl-3-furyl-methyl (1R, 3S, E) 2,2-dimethyl-3-(2-oxo-2,3,4,5-tetrahydro-3-thienylidenemethyl)-cyclopropane-1-carboxylate, (RS)α-cyano-3-phenoxybenzyl (1R, cis) 2,2-dimethyl-3-(2,2-dibromovinyl)cyclopropane-1-carboxylate, α-cyano-3-phenoxy-benzyl 2-(4-chlorophenyl)-3-methyl-butyrate and (S)α-cyano-3-phenoxybenzyl (1R, cis) 2,2-dimethyl-3-cyclopentylidenemethyl-cyclopropane-carboxylate.

The compounds of formula II are known from French Pat. No. 1,503,260, No. 2,241,533 and No. 2,185,612 for example and are known to possess interesting pesticidal activity such as insecticidal, acaricidal, nematocidal and fungicidal activity. Some of the compounds of formula II possess only one of the said activities while other possess a plurality of the totality of the said activities. Until now, the said compounds have been administered to warm-blooded animals to protect them from parasites by standard methods such as topically, parenterally or digestively.

The present invention resides in the fact that it is possible to obtain excellent results against animal parasites by administering the compounds of formula I by the method which could be described as a "pour on" method. This method consists of painting a small surface of the animal's body, preferably the dorsal spine thereof, with a solution of the active compound to obtain an activity over the entire body of the animal. This method is not a general one and is not susceptible to be applied with chemical compounds capable of varying in their activity during the migration.

Tests have clearly shown that it is possible to suppress all the ticks, larvae and nymphs as well as all the lice of an infested animal by the method of the invention and that the action is very rapid and very durable.

The teachings of the prior art would not suggest to one skilled in the art the use of the said compounds by this method. The method of the invention is not only unobvious, it also has the unexpected ability to obtain excellent results very rapidly and for a prolonged period of time with very small amounts of the compounds of formula I and II which makes the method of great commercial interest. The method of treatment permits a simple, proper and economical application of the compounds of formula I and II and the advantages of such a "pour on" method to one skilled in the art would be obvious from the classical methods of administration.

The administration of the compounds of formulae I or II by the digestive route, i.e. orally or rectally, gives good results but this route has always the possibility of causing gastric troubles and is, moreover, reserved for combatting parasites situated in the stomach. The administration by baths also gives good results but unfortunately this requires the use of very large quantities of the active material making it necessary to renew often the bath the pyrethrinoids which generally are easily decomposed. The parenteral administration of the compounds is to be avoided each time when it is possible as it is not easy to give an injection to all animals of a herd.

The "pour on" method of the invention may be used to apply the compounds of formulae I and II to all warm-blooded animals and especially to breeding animals such as bovines, sheep and pigs for example as well as the domestic animals such as cats and dogs. The treatment method of the invention is useful for treating internal and external parasites and is particularly useful against acariens such as ticks and scabies, Helminths, varron, insects such as lice, bugs and differenrt sorts of stinging flies.

The appropriate vehicles for the treatment of animals by the method of the invention are preferably oily solutions, alcoholic solutions such as ethanol or isopropanol solutions, solutions in esters of monocarboxylic acids such as isopropyl myristate or of dicarboxylic acids or solutions of esters of aliphatic acids generally with glycols. The solutions preferably contain a dispersant product such as dimethylformamide, dimethylsulfoxide or dimethylacetamide or any other dispersant agent known in the pharmaceutical industry as far as great the solubility of the products of formula I or II is permitted in the agents such as for example, pyrrolidine-2-one, N-alkyl-pyrrolidine-2-ones, methyl ethyl ketone, acetone, polyethyleneglycols and their ethers and esters, propyleneglycol and synthetic triglycerides.

The oily solutions are preferably based on vegetable oils such as olive oil, arachide oil, sesame oil, pine oil, linseed oil or castor oil. In a particularly preferred embodiment of the method of treating warm-blooded animals, the vehicle is an oil solution containing dimethylformamide.

The amount of the compound of formulae I or II used varies as a function of the state of the animal to be treated, their species, their environment as well as the condition being treated. Generally, the compositions contain 1 to 5% by weight of at least one compound of formulae I or II, 0.1 to 50% by weight of the dispersing agent and 98.9 to 45% by weight of solvent.

The method of the invention for treating warm-blooded animals preferably uses 0.5 to 10 mg of the compound of formulae I or II per kg of weight of the treated animal. The number of treatments will also vary due to the parameters discussed above to determine the amount of compound to be administered but tests have shown that excellent results can be obtained with a single painting.

The compositions used in the method of the invention permit the treatment of the entire body of the animals with the products of formulae I or II by application in the form a solution in a suitable vehicle to only a part of the surface of the animals body and preferably to a part of the dorsal spine.

Some preferred compositions of the invention have as the active ingredient at least one compound of the formula

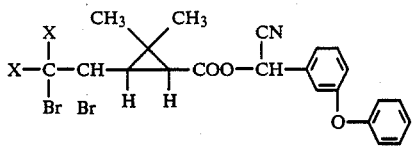

wherein X is selected from the group consisting of chlorine and bromine, (S)α-cyano-3-phenoxy-benzyl (1R, cis) 2,2-dimethyl-3-(2,2-dichloro-1,2-dibromoethyl)-cyclopropane-1-carboxylate called product A in the Examples and (S)α-cyano-3-phenoxy-benzyl (1R, cis) 2,2-dimethyl-3-(1,2,2,2-tetrabromoethyl)-cyclopropane-1-carboxylate are two preferred compounds.

In the following examples there are described several preferred embodiments to illustrate the invention. However, it should be understood that the invention is not intended to be limited to the specific embodiments.

EXAMPLE 1

The antiacarien activity of (S)α-cyano-3-phenoxy-benzyl 1R, cis 2,2-dimethyl-3-(2,2-dichlorovinyl)-cyclopropane-1-carboxylate (product B) was determined on calves infected with *Boophilus microplus* ticks which were in various states of development. The dorsal spine of the calves was painted on day J with a solution containing either 5 or 10 mg of product B per kg of animal weight. The number of living ticks was determined on day J before treatment and days J+1, J+2, J+4 and J+7 and the presence of or absence of larvae and nymphs was also determined. The results are reported in Table I.

TABLE I

| Day | Dose in mg/kg | No. of ticks |
|---|---|---|
| J | 5 | 123 adult ticks + numerous larvae + nymphs |
|  | 10 | 61 adult ticks + numerous Larvae + nymphs |
| J + 1 | 5 | 2 adult ticks + larvae + nymhs |
|  | 10 | 3 adult ticks + larvae + nymphs |
| J + 2 | 5 | 0 adult ticks, larvae & nymphs |
|  | 10 | 0 adult ticks, larvae + nymphs |
| J + 4 | 5 | 0 adult ticks, larvae + nymphs |
|  | 10 | 0 adult ticks, larvae + nymphs |
| J + 7 | 5 | 0 adult ticks, no larvae or nymphs |
|  | 10 | 0 adult ticks, no larvae or nymphs |

The result of Table I show that product B has an excellent activity against ticks of the *Boophilus microplus* strain.

EXAMPLE 2

The insecticidal activity of (S)α-cyano-3-phenoxy-benzyl 1R, cis 2,2-dimethyl-3-(2,2-dibromovinyl)-cyclopropane-1-carboxylate (product A) against bovine lice was determined on bovines infested therewith. The dosal spine of each animal was painted only once with 40 ml of a solution containing 0.5% of product A and very good insecticidal results were obtained.

EXAMPLE 3

The antiacarien activity of (S)α-cyano-3-phenoxy-benzyl 1R, cis 2,2-dimethyl-3-cyclopentylidenemethyl-cyclopropane-1-carboxylate (product C) was determined by the method of Example 1 on bovines artificially infested with Mexican ticks in all stages of development. Two bulls were treated with 5 mg/kg each, two were treated with 2.5 mg/kg each and two were untreated to serve as controls. The reduction in the number of ticks was determined in the treated animals as a percentage in relation the control animals and the results are reported in Table II.

TABLE II

| Dose in mg/kg | No. of ticks | % reduction of ticks |
|---|---|---|
| 0 | 20,131 | — |
| 2.5 | 3,886 | 80.7 |
| 5.0 | 1,745 | 91.3 |

The results of Table II show that product C has a very remarkable activity against ticks.

EXAMPLE 4

The tolerance of cows to product A was determined by painting the dorsal spine thereof with a solution containing 50 g per liter of product A and a local examination was made thereof after 10 days. It was observed that product A was perfectly well tolerated.

EXAMPLE 5

Compositions were prepared containing 1700 mg of product B, 40 ml of dimethylformamide and 40 ml of olive oil.

EXAMPLE 6

Test against *Boophilus microplus*

A young bull weighing 340 kg was voluntarily infested with ticks of the *Boophilus microplus* species wherein the ticks were all in the first stage of development. The dorsal spine of the animal was painted on day J with a solution of 1.7 g of (S)α-cyano-3-phenoxy-benzyl (1R, cis) 2,2-dimethyl-3-(2,2-dichloro-1,2-dibromoethyl)-cyclopropane-1-carboxylate (product A) in 80 ml of a 1-1 dimethylformamide-olive oil mixture at a rate of 5 mg of Product A per kg of the treated bull. The number of ticks and their stage of development was determined at the days indicated in Table III.

TABLE III

|  | Days before and after treeatment ||||||| 
|  | J-2 | J-1 | J | J + 1 | J + 2 | J + 3 | J + 4 |
|---|---|---|---|---|---|---|---|
| No. of ticks | 16 | 21 | 71 | 13 | 13 | 0 | 0 |
| % inhibition of egg laying | 0 | 0 | 0 | 38 | 23 | — | — |
| Stage of Development |  |  | first stage of development || the ticks were alive but partly dead || all the ticks were dead ||

The results of Table III show that Product A has a remarkable tickicide activity.

EXAMPLE 7

Tests against Mexican strain of *Boophilus microplus*

Young bulls were voluntarily infested with *Boophilus microplus* ticks and a control group received no treatment while a second group were painted on day J wih 100 ml of a solution identical to that of Example 1 at the rate of 5 mg of product A per kg of treated bull. The number of ticks before and after the treatment was compared for the treated and not treated bulls and the results are reported in Table IV.

TABLE IV

Number of Ticks phenol polyethyleneglycol) was administered in a volume of 40 or 30 ml at a dose of 5, 2.5 or 1 mg/kg of the treated animals. The number of ticks before and after treatment was determined and compared for the treated and untreated animals to determine the percent of activity. The results are reported in Table V.

TABLE V

| Dose of Product A | NUMBER OF TICKS | | | | | | | |
|---|---|---|---|---|---|---|---|---|
| | 5 mg/kg (40 cm3) | | 2,5 mg/kg (30 cm3) | | 1 mg/kg (30 cm3) | | Control group | |
| | 1 | 2 | 3 | 4 | 5 | 6 | 7 | 8 |
| J − 3 | 1 | 0 | 0 | 0 | 0 | 0 | 0 | 0 |
| J − 2 | 136 | 0 | 23 | 0 | 21 | 10 | 36 | 0 |
| J − 1 | 320 | 0 | 234 | 0 | 103 | 26 | 128 | 0 |
| J | | | Day of Treatment | | | | | |
| J + 1 | 2 | 0 | 7 | 0 | 26 | 8 | 63 | 5 |
| 2 | 0 | 0 | 4 | 0 | 2 | 3 | 2 | 0 |
| 3 | 0 | 0 | 1 | 6 | 4 | 0 | 38 | 1 |
| 4 | 1 | 0 | 7 | 0 | 12 | 1 | 262 | 5 |
| 5 | 2 | 0 | 1 | 0 | 8 | 1 | 67 | 2 |
| 6 | 0 | 0 | 1 | 0 | 1 | 3 | 11 | 2 |
| 7 | 0 | 0 | 1 | 0 | 1 | 4 | 3 | 11 |
| 8 | 0 | 0 | 0 | 0 | 0 | 2 | 8 | 10 |
| 9 | 0 | 0 | 0 | 0 | 1 | 2 | 1 | 3 |
| 10 | 1 | 0 | 0 | 0 | 0 | 1 | 11 | 6 |
| 11 | 0 | 0 | 0 | 0 | 0 | 0 | 67 | 65 |
| 12 | 0 | 0 | 0 | 0 | 1 | 2 | 44 | 27 |
| 13 | 0 | 0 | 0 | 0 | 1 | 0 | 29 | 35 |
| 14 | 0 | 0 | 0 | 0 | 0 | 2 | 39 | 39 |
| 15 | 0 | 0 | 0 | 0 | 2 | 7 | 74 | 21 |
| 16 | 0 | 0 | 0 | 0 | 1 | 0 | 4 | 6 |
| 17 | 0 | 0 | 0 | 0 | 0 | 2 | 16 | 9 |
| 18 | 0 | 0 | 0 | 0 | 0 | 0 | 43 | 49 |
| 19 | 0 | 0 | 0 | 0 | 0 | 3 | 103 | 39 |
| 20 | 0 | 0 | 0 | 0 | 0 | 2 | 40 | 10 |
| 21 | 0 | 0 | 0 | 0 | 0 | 3 | 7 | 1 |
| 1–21 | 6 | 0 | 22 | 0 | 60 | 46 | 932 | 346 |

| Day | Product A-5 mg/kg | | | Control Group | | |
|---|---|---|---|---|---|---|
| | 1 | 2 | 3 | 1 | 2 | 3 |
| J − 2 | 3 | 3 | 1 | 2 | 1 | 3 |
| J − 1 | 99 | 80 | 172 | 106 | 76 | 64 |
| 0 | Day of Treatment | | | | | |
| 1 | 53 | 60 | 50 | 152 | 94 | 525 |
| 2 | 4 | 0 | 2 | 38 | 28 | 306 |
| 3 | 0 | 1 | 4 | 47 | 27 | 101 |
| 4 | 10 | 0 | 1 | 128 | 81 | 82 |
| 5 | 4 | 0 | 0 | 97 | 76 | 165 |
| 6 | 0 | 0 | 0 | 21 | 71 | 125 |
| 7 | 1 | 0 | 1 | 116 | 96 | 173 |
| 8 | 1 | 0 | 0 | 57 | 60 | 145 |
| 9 | 0 | 0 | 0 | 31 | 19 | 75 |
| 10 | 0 | 0 | 0 | 77 | 127 | 49 |
| 11 | 0 | 0 | 0 | 174 | 200 | 111 |
| 12 | 1 | 0 | 0 | 60 | 87 | 144 |
| 13 | 1 | 0 | 0 | 339 | 242 | 114 |
| 14 | 0 | 0 | 0 | 450 | 378 | 75 |
| 15 | 0 | 0 | 0 | 166 | 96 | 67 |
| 16 | 0 | 0 | 0 | 36 | 18 | 27 |
| 17 | 0 | 0 | 0 | 41 | 5 | 103 |
| 18 | 0 | 0 | 0 | 636 | 92 | 960 |
| 19 | 1 | 0 | 0 | 601 | 291 | 1076 |
| 20 | 0 | 0 | 0 | 133 | 242 | 316 |
| 21 | 0 | 0 | 0 | 12 | 137 | 29 |
| 1–21 | | 195 | | | 10644 | |
| Efficacicy | | 98.2 | | | = 0 | |

Again, the results of Table IV show that Product A has a remarkable activity against ticks.

EXAMPLE 8

8 young bulls were voluntarily infested with larvae of *Boophilus microplus* (sensible Mexican strain) so that at the moment of treatment the ticks were in the first stage of development. Product A in solution in a mixture of 85 g of dimethylformamide, 7 g of Emulsogen (emulsifier for oils, paraffins or organic solvents) and 3 g of Arcopal (surface active agent of a non-ionic alkyl-phenol polyethyleneglycol) was administered in a volume of 40 or 30 ml at a dose of 5, 2.5 or 1 mg/kg of the treated animals. The number of ticks before and after treatment was determined and compared for the treated and untreated animals to determine the percent of activity. The results are reported in Table V.

The percentage of efficacy of Product A at 5, 2.5 and 1 mg/kg was found to be 99.4%, 97.6% and 94.3%, respectively. The results show that Product A has a remarkable activity.

EXAMPLE 9

Young bulls were strongly infested naturally with a plurality of *Rhipicephalus appendiculatus*, *Rhipicephalus evertsi*, *Rhipicephalus simus*, *Amblyomma hebraeum* and *Hyalomma* Species and product A was administered as in Example 1 at doses of 5, 2.5 and 1 mg/kg of treated animal and the results on days J+1, J+2 and J+3 are reported in Table VI.

TABLE VI

| No of animal | Doses in mg/kg | Weight Corporal (KG) | Before Treatment | Number of Ticks Day of test following treatment | | |
|---|---|---|---|---|---|---|
| | | | | 1 | 2 | 3 |
| 1 | 5 | 40 | >200 | 2 | 10 | 9 |
| 2 | 5 | 40 | >200 | 0 | 10 | 6 |
| 3 | 5 | 40 | >200 | 0 | 10 | 6 |
| 4 | 2.5 | 40 | >200 | 1 | 15 | 2 |
| 5 | 2.5 | 80 | >200 | 0 | 5 | 2 |
| 6 | 2.5 | 40 | >100 | 0 | 6 | 0 |
| 7 | 1 | 40 | >200 | 6 | 10 | 19 |
| 8 | 1 | 230 | >200 | 0 | 31 | 12 |
| 9 | 1 | 270 | >200 | — | 42 | 41 |
| 10 | 1 | 110 | >100 | 2 | 9 | 7 |
| 11 | 1 | 130 | >200 | 9 | — | 3 |
| 12 | 1 | 240 | >200 | 0 | 24 | 10 |
| 13 | 1 | 130 | >100 | 0 | 0 | 6 |

The results of Table VI show that product A has a remarkable activity against natural infestation of a variety of different species of ticks.

EXAMPLE 10

This test was effected in Africa with adult cows and about 8 month old calves covered with ticks and the animals were treated by painting of the dorsal spine with a solution of Product A at a dose of 4, 5 or 10 mg per kg of treated animal. The number of ticks was determined on J, the day of treatment, and the following three days and the results are reported on Table VII.

TABLE VII

| Treated Animal | Weight of animal in kg | Dose in mg/kg | Applied Volume in ml | Number of ticks on day | | | |
|---|---|---|---|---|---|---|---|
| | | | | J | J + 1 | J + 2 | J + 3 |
| Adult cow | 300 | 4 | 20 | 68/N: + | 0 | 1 | 3 |
| Calf | 120 | 5 | 10 | 71/N: ++++ | 0 | 4 | 1 |
| Calf | 156 | 10 | 26 | 153/N: ++++ | 0 | 3 | 1 |

N = Nymphs only in the folds of the ears

Table VII shows that Product A has a remarkable activity against ticks.

EXAMPLE 11

A tickicidal composition was prepared containing 1.7 g of product A, 40 ml of dimethylformamide and 40 ml of olive oil and a similar composition was prepared containing 1.6 g of Product A, 85 ml of dimethylformamide, 7 g of Emulsogen and 3 g of Arcopal.

Various modifications of the compositions and method of the invention may be made without departing from the spirit or scope thereof and it should be understood that the invention is intended to be limited only as defined in the appended claims.

What we claim is:

1. A method of killing insects and acariens on infested breeding animals comprising applying to a portion of the dorsal spine of the infested breeding animal's body a lethal composition consisting essentially of an isomeric form of an active compound of the formula

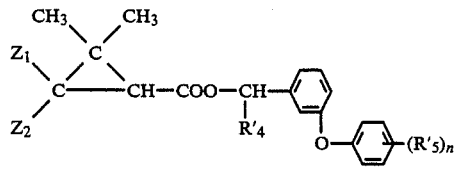

wherein $Z_1$ and $Z_2$ are both methyl or $Z_1$ is hydrogen and $Z_2$ is

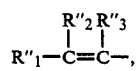

$R_3''$ is selected from the group consisting of hydrogen and halogen and $R_1''$ and $R_2''$ are individually selected from the group consisting of halogen and alkyl of 1 to 8 carbon atoms, $R_4'$ is selected from the group consisting of —CN and —C≡CH, $R_5'$ is selected from the group consisting of methyl and chlorine and n is 0, 1 or 2 in an appropriate vehicle, the amount of active compound used is 0.5 to 10 mg per kg of animal weight.

2. The method of claim 1 wherein $R_3''$ is hydrogen.

3. The method of claim 2 wherein $R_1''$ and $R_2''$ are halogen.

4. The method of claim 3 wherein $R_1''$ and $R_2''$ are bromine or chlorine.

5. The method of claim 1 wherein the active ingredient is (S)α-cyano-3-phenoxy-benzyl 1R, cis 2,2-dimethyl-3-(2,2-dichlorovinyl)-cyclopropane-1-carboxylate.

6. The method of claim 1 wherein the active ingredient is (S)α-cyano-3-phenoxy-benzyl 1R, cis 2,2-dimethyl-3-(2,2-dibromovinyl)-cyclopropane-1-carboxylate.

7. The method of claim 1 wherein the active ingredient is 3-phenoxy-benyl 1R, trans 2,2-diethyl-3-(2,2-dichlorovinyl)-cyclopropane-1-carboxylate.

8. The method of claim 1 wherein the active ingredient is (RS)α-cyano-3-phenoxy-benzyl 1R, cis 2,2-dimethyl-3-(2,2-dichlorovinyl)-cyclopropane-1-carboxylate.

9. The method of claim 1 wherein the active ingredient is (RS)α-cyano-3-phenoxy-benzyl 1R, cis 2,2-dimethyl-3-(2,2-dibromovinyl)-cyclopropane-1-carboxylate.

10. The method of claim 1 wherein the vehicle is an oil solution.

11. The method of claim 10 wherein the oil solution contains dimethylformamide.

12. The method of claim 1 wherein the parasites are acariens.

13. The method of claim 1 whrerin the active compound is selected from the various possible iosmers of a compound of the formula

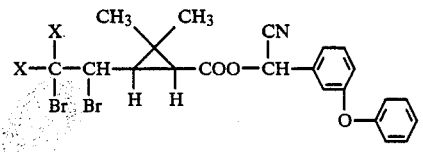

wherein X is selected from the group consisting of chlorine and bromine.

14. The method of claim 1 wherein the active compound is (S)α-cyano-3-phenoxy-benzyl (1R, cis) 2,2-dimethyl-3-(2,2-dichloro-1,2-dibromoethyl)-cyclopropane-1-carboxylate.

15. The method of claim 1 wherein the active compound is (S)α-cyano-3-phenoxy-benzyl (1R, cis) 2,2-dimethyl-3-(1,2,2,2-tetrabromoethyl)-cyclopropane-1-carboxylate.

16. The method of claim 1 wherein the vehicle is an oil solution containing 0.1 to 5% by weight of a dispersant selected from the group consisting of dimethylformamide, dimethylsulfoxide and dimethylacetamide and contains 1 to 5% by weight of the active compound.

17. The method of claim 16 wherein the vehicle is dimethylformamide in a vegetable oil.

18. The method of claim 1 wherein the animals are selected from the group consisting of bovines, sheep and pigs.

* * * * *